US00PP13044P2

(12) United States Plant Patent
Bessho

(10) Patent No.: US PP13,044 P2
(45) Date of Patent: Oct. 1, 2002

(54) CALIBRACHOA PLANT NAMED 'KAKEGAWA S27'

(75) Inventor: Masao Bessho, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/709,938

(22) Filed: Nov. 13, 2000

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Rothwell, Figg, Ernst & Manbeck

(57) ABSTRACT

Disclosed herein is a new and distinct Calibrachoa plant, and its parts, named 'Kakegawa S27' having a creeping plant habit, abundant branching and light yellow petal colors.

1 Drawing Sheet

BACKGROUND OF THE NEW PLANT

This invention relates to a new and distinct cultivar of Calibrachoa plant, hereinafter referred to by the name 'Kakegawa S27'. 'Kakegawa S27' is a new variety of Calibrachoa plant having a creeping, branching habit. The plant grows vigorously and makes an excellent hanging basket. The invention's flowers are funnel shaped with five-fissured limbs, and a slight indent on each petal. The flowers are single with a diameter of 3.0–3.2 cm when fully open. At petal opening the petals are light yellow (RHS 6D) with a darker yellow corolla tube (RHS 7A). The petals will fade in the sun to a yellowish white (RHS 8D) color. The plant grows and flowers best under low soil pH conditions (pH 5–6). Typically young flowers will close under low light and low temperature conditions such as late in the day or at night.

The genus Petunia was originally established in 1803 by A. L. Jussieu, who described both *P. parviflora* and *P. nyctaginfloa* as type species. Using a non-horticultural system that selected the first mentioned species as the type species (lectotype), N. L. Britton and H. A. Brown declared *P. parviflora* as the type species for Petunia in 1913.

During the 1980's and 1990, H. J. Wijsman published a series of articles regarding the ancestry of *P. hybrida*, the Garden Petunia, and the inter-relationship of several species classified as Petunia. These studies revealed that *P. hybrida* and its ancestral species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the Petunia genus, Wijsman and J. H. deJong proposed transferring the 14 chromosome species to the genus Stimoryne. Horticulturists opposed reclassifying the Garden Petunia and in 1986, Wijsman proposed the alternative of making *P. nyctaginiflora* the lectotype species for Petunia and transferring the 18 chromosome species to another genus. The I.N.G. Committe adopted this proposal. By 1990 Wijsman had transferred several species, including *P. parviflora* (=*C. parviflora*) to Calibrachoa, originally established by Llave and Lexarza in 1825. *Calibrachoa*

*parviflora* (=*C. mexicana la Lave & Lexarza*) is now the type species for the genus Calibrachoa.

Classification of the current Petunia and Calibrachoa species is still in progress. New species are also being identified. Consequently a proper description has not been written for the Calibrachoa genus. Calibrachoa can, however, be distinguished from Petunia based on the higher chromosome number, chromosome morphology, plant branching habit and type of flower bud estivation. Whereas, Petunia species bear a flower peduncle and one new stem from a node, Calibrachoa bear a flower peduncle and three stems. Petunia species have a cochlear corolla bud, a single outermost petal covers the other four, radially folded and terminally contorted petals. Calibrachoa flower buds are flat with all five petals linearly folded and the two lower petals forming a cover around the three other petals and fused together.

Asexual reproduction of 'Kakegawa S27' Calibrachoa originated from a hybridization made in 1996 by the Sakata Seed Corporation, Kakegawa breeding station in Kakegawa, Japan. The female parent was a breeding line known only as 'White #1'. The male parent was a breeding line known only as '5B-133B'. The initial cross-pollination of the parents, resulting in $F_1$ generation seed, was made in May, 1998. In August, 1998, the $F_1$ seed was sown in the field at Kakegawa. That summer one plant was selected for nice color and a creeping, branching habit. This plant was asexually reproduced and grown in the greenhouse the following winter. In February, 1999 these liens were selected and propagated again for evaluation. Trait stability was confirmed that summer in the greenhouses in Kakegawa, Japan.

In the Summer of 1999, cuttings of this plant line were sent California. During this Summer plants were grown under the direction and supervision of the inventor for evaluation of stability of the line's desired traits. Plants were evaluated in hanging pots at the research station in Salinas, Calif. Final selection of one line as the new variety was made in California. The present invention, 'Kakegawa S27' Calibrachoa was determined by the inventor to have it's characteristics, as herein described, firmly fixed.

The plant was asexually produced by excising the terminal 1.0 to 1.5 inches of an actively growing stem. The basal half is stripped of leaves and dipped in a 1:19 diluton of Dip-N-Gro™ rooting solution (solution:water). Plastic cell trays with a 1.0 inch diameter by 1.5 inch deep cells are filled with a peat-moss based growing media. The basal portion of the stem is then inserted into moistened peat-moss media. The cuttings are kept in a warm greenhouse under a clear plastic tent with occasional misting from an automatic watering system. The cuttings are fully rooted in six weeks.

BRIEF DESCRIPTION OF THE DRAWINGS

The accompanying drawings serve by color photographic means to illustrate the new plant variety, 'Kakegawa S27'. The colors are represented as true as possible using conventional photographic procedures.

DETAILED DESCRIPTION OF THE NEW VARIETY

Figure 1:
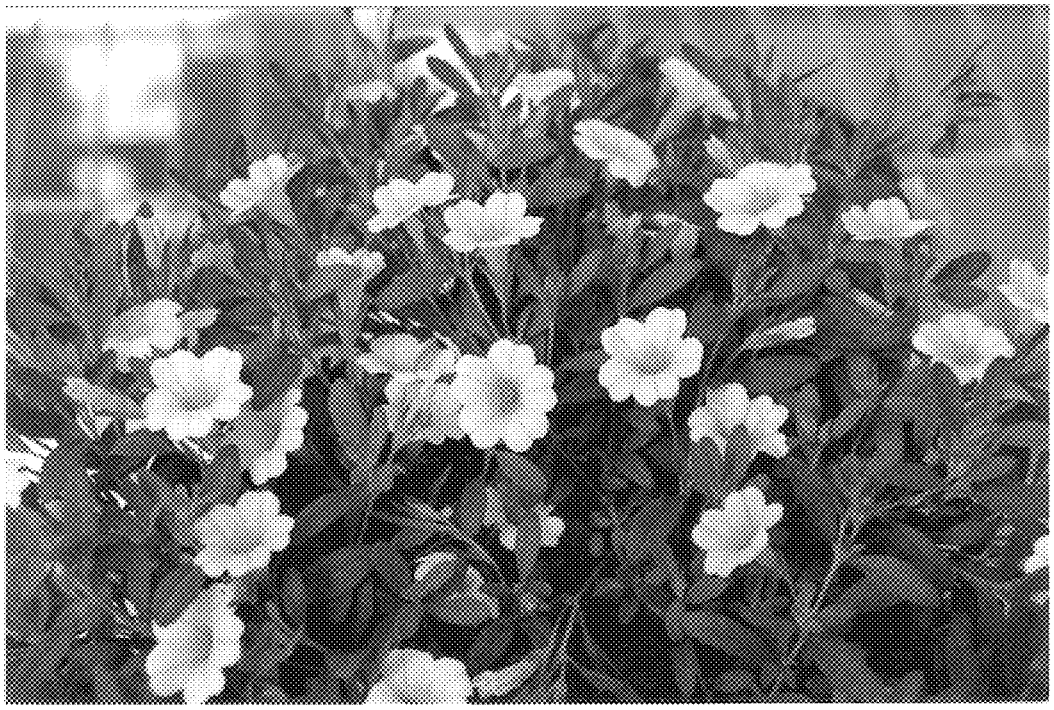
FIG. 1 is a close-up view of multiple blooms illustrating the creeping habit; abundant branching; large profusion of blooms and flower morphology.
Figure 2:
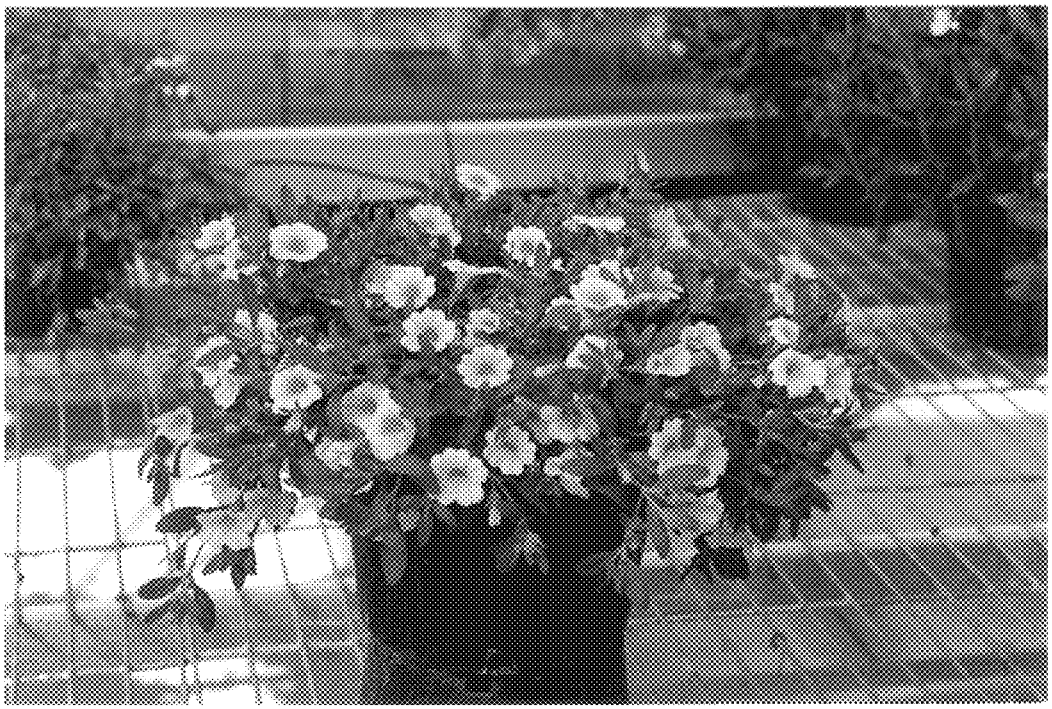
FIG. 2 is a view of the new cultivar after growing for several weeks in a six-inch greenhouse pot.

The following description is based on observations and measurements of pot grown plants in Salinas, Calif. Data was collected on plants six weeks after individually transplanting rooted cuttings to a six inch pot. Color designations were made according to The Royal Horticultural Society Colour Chart (R.H.S.) published by The Royal Horticultural Society of London, England.

Origin: Seedling.

Parentage: This new variety is a selection from the $F_2$ progeny of three intercrossed $F_1$ plants derived from the cross of 'Liricashower Rose' (U.S. Plant Pat. No. 9,884) with Breeding Line 'White #1' (an unpatented plant).

Classification:
- *Family.*—Solanaceae.
- *Genus.*—Calibrachoa.
- *Botanical.*—Calibrachoa sp.
- *Commercial.*—'*Kakegawa S27*'.

Plant:
- *Growth habit.*—Creeping; strongly branching.
- *Plant height.*—Varies depending on the container size; a hanging basket measuring 40 cm in diameter will produce a plant 40 to 50 cm in length and 70 to 90 cm in width.
- *Time to produce a rooted cutting.*—Six weeks for full root development in a plastic cell tray with 1.0 inch diameter by 1.5 inch deep cells.
- *Life cycle.*—Perennial.

Stem:
- *Thickness.*—1.0 mm.
- *Color.*—Light green (144C).
- *Pubescence.*—Slight.
- *Branching.*—Abundant.
- *Internode length.*—1.0–3.0 cm.

Leaf:
- *Apex.*—Mucronate.
- *Base.*—Oblique.
- *Arrangement.*—Verticillate.
- *Color.*—Upper leaf color is green RHS 137A; lower leaf color is green RHS 137B.
- *Pubescence.*—Moderate on upper and lower surfaces; pubescence is short, colorless and bulbous at the tip.
- *Fragrance.*—None.
- *Shape.*—Elliptic.
- *Length* (*average*).—4.2 cm at full expansion.
- *Margin.*—Entire.
- *Surface.*—Slightly pubescent; dull.
- *Variegation.*—None.
- *Venation.*—Pinnate.
- *Width* (*average*).—1.5 cm at full expansion.

Flower:
- *Blooming period.*—Plants bloom with long days starting in March and continuing into October. Each bloom lasts three days. Blooms stay open all day and night. Blooms are fairly cold tolerant but will not withstand freezing temperatures.
- *Quantity.*—Mature plants growing in a six inch diameter pot can have in excess of 100 open flowers. The inflorescence is solitary.
- *Calyx.*—5 sepals; 1.5 cm length×0.4 cm width.
- *Corolla.*—5 petals; fused.
- *Diameter.*—3.0–3.2 cm.
- *Shape.*—The flowers are funnel shaped with five fissures and a shallow, yet prominent, indentation of the petal tip at the midvein. Flower depth is approximately two-thirds of flower diameter or 1.3–1.6 cm. Petal fusion is invisible and has a length of 1.0–1.2 cm.
- *Fragrance.*—None.
- *Habit.*—Indeterminate.
- *Inflorescence type.*—Solitary.
- *Ovary.*—Superior.
- *Pedicel length.*—1.6–2.2 cm.
- *Stamen color.*—Yellow RHS 6D anthers.
- *Stigma color.*—Green RHS 143C.
- *Style color.*—Green RHS 143C.
- *Placenta arrangement.*—Central.
- *Petal pubescence.*—Glabrous.
- *Petal color.*—Upper petal surface is RHS 6D (light yellow) at the corolla throat fading to 8D (yellowish white) at the petal tips with RHS 13B (yellow-orange) midveins; lower petal surface is RHS 6B (yellow) with RHS 13B (yellow-orange) midveins; corolla tube inner surface is RHS 7A (yellow); outer surface is RHS 6B (yellow).
- *Petal size.*—2.0–2.5 cm length×1.1–1.3 cm width.
- *Pollen color.*—RHS 3C (yellow).
- *Stamens.*—5.
- *Fruit & seeds.*—No seeds or fruits are produced.

Disease/pests: Plants are susceptible to Botrytis, powdery mildew, various stem and root rots and certain viruses like Tobacco Mosaic Virus and Impatiens Necrotic Spotted Virus. Plants can be infested with aphids, leafminer, whitefly and various Lepitopdera. Plants are cold tolerant and can overwinter under snow cover.

Comparison With Other Known Varieties

The new variety is distinguished from other Calibrachoa plants by its light yellow petal color and creeping habit. The closest commercial cultivar to this new variety that we are aware of is the petunia-like plant named 'Million Bells Trailing White'. The distinguishing characteristics which differentiate 'Kakegawa S27' from 'Million Bells Trailing White' are:

| | 'Kakegawa S27' | 'Million Bells Trailing White' |
|---|---|---|
| Plant Habit | Creeping | Mounding |
| Internode Length | 1.0–3.0 cm | 0.5–1.8 cm |
| Flower Color | Light yellow at opening fading to yellowish white with a yellow corolla tube | Pure white with a pale yellow corolla tube and yellow mid veins |

-continued

| | 'Kakegawa S27' | 'Million Bells Trailing White' |
|---|---|---|
| Flower Size | 3.0–3.2 cm | 2.0–3.0 cm |
| Leaf Length | 4.2 cm | 3.2 cm |

We claim:

1. A new and distinct cultivar of Calibrachoa plant herein referred to by the name 'Kakegawa S27', substantially as herein illustrated and described.

* * * * *